United States Patent
Ishikawa et al.

(10) Patent No.: US 10,030,039 B2
(45) Date of Patent: Jul. 24, 2018

(54) ANTI-CANCER AGENT AND CANCER CELL KILLING METHOD

(71) Applicants: IHI Corporation, Tokyo (JP); Yoshihiro Ishikawa, Tokyo (JP)

(72) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 0 days.

(21) Appl. No.: 15/468,462

(22) Filed: Mar. 24, 2017

(65) Prior Publication Data

US 2017/0240581 A1    Aug. 24, 2017

Related U.S. Application Data

(63) Continuation of application No. PCT/JP2014/075745, filed on Sep. 26, 2014.

(51) Int. Cl.

| | | |
|---|---|---|
| *A61K 31/28* | (2006.01) | |
| *A61K 31/16* | (2006.01) | |
| *A61K 31/18* | (2006.01) | |
| *A61K 31/15* | (2006.01) | |
| *A61K 31/135* | (2006.01) | |
| *C07F 15/02* | (2006.01) | |
| *A61K 33/00* | (2006.01) | |
| *A61K 33/04* | (2006.01) | |
| *A61K 33/24* | (2006.01) | |
| *A61K 33/32* | (2006.01) | |

(52) U.S. Cl.
CPC ............ *C07F 15/025* (2013.01); *A61K 31/28* (2013.01); *A61K 33/00* (2013.01); *A61K 33/04* (2013.01); *A61K 33/24* (2013.01); *A61K 33/32* (2013.01)

(58) Field of Classification Search
CPC ........ A61K 31/28; A61K 33/00; A61K 33/32; A61K 33/24
USPC ............... 424/600, 604, 639, 646, 649, 655; 514/492, 505
See application file for complete search history.

(56) References Cited

U.S. PATENT DOCUMENTS

| | | |
|---|---|---|
| 5,549,915 A | 8/1996 | Volkonsky et al. |
| 2004/0047852 A1 | 3/2004 | Kennedy |
| 2009/0169484 A1 | 7/2009 | Eguchi et al. |
| 2012/0029167 A1 | 2/2012 | Ishikawa et al. |
| 2014/0046021 A1 | 2/2014 | Ishikawa et al. |

FOREIGN PATENT DOCUMENTS

| | | |
|---|---|---|
| JP | 2001-010978 A | 1/2001 |
| JP | 2012-167067 A | 9/2012 |
| JP | 2014-210742 A | 11/2014 |
| WO | 01/80849 A1 | 11/2001 |
| WO | 2010/058280 A1 | 5/2010 |
| WO | 2012106514 A2 | 8/2012 |

OTHER PUBLICATIONS

Sato, et al., "Hyperthermia generated with ferucarbotran (Resovist) in an alternating magnetic field enhances cisplatin-induced apoptosis of cultured human oral cancer cells", J Physiol Sci., Mar. 2014, vol. 64:177-183.
International Search Report from International Application No. PCT/2014/075745 dated Dec. 22, 2014.
Meshkini, et al., "Chemosensitization of human leukemia K562 cells to taxol by a vanadium-salen complex", Experimental and Molecular Pathology 89 (2010) 334-342.
Search Report for SG Application No. 11201702260R dated Feb. 14, 2018, 9 pages.
JP Office Action dated Mar. 20, 2018 directed to the JP Application No. 2016-549888, 7 pages.

*Primary Examiner* — Raymond J Henley, III
(74) *Attorney, Agent, or Firm* — Brundidge & Stanger, P.C.

(57) ABSTRACT

[Object] An anticancer agent capable of continuously killing cancer cells in a plurality of phases is provided.
[Solution] An anticancer agent contains a complex produced by making a metal-salen complex compound, which includes a central metal and (N, N, O, O) as a quadridentate ligand and is magnetic, bind to taxane molecules which are anticancerous; and the anticancer agent is to kill cancer cells regarding which phase transition of its cell cycle occurs between phases including Gap1, Synthesis, Gap2, and Mitosis and Cytokinesis. The present disclosure is suited for use to kill cancer cells of breast cancer and, particularly, cancer cells of triple-negative breast cancer. The present disclosure is designed to make the anticancer agent contact the cancer cells in two or more continuous phases selected from a group consisting of Gap1, Synthesis, Gap2, and Mitosis and Cytokinesis and kill the cancer cells.

9 Claims, 11 Drawing Sheets

ANTI-CANCER AGENT AND CANCER CELL KILLING METHOD

TECHNICAL FIELD

The present disclosure relates to an anti-cancer agent. Particularly, the disclosure relates to an anti-cancer agent and cancer cell killing method for killing cancer cells of triple-negative breast cancer.

BACKGROUND ART

A taxane-type anti-cancer agent is an anti-cancer agent for inhibiting division of cancer cells and inducing apoptosis and has excellent therapeutic effects by being made to contact the cancer cells in Gap2 (G2 phase) through mitosis and cytokinesis (M phase). However, the cancer cell killing effect of the taxane-type anti-cancer agent is low in Gap0 (G0 phase) and Gap1 (G1 phase) and growth of the cancer cells in the G1 phase cannot be inhibited. Moreover, when the taxane-type anti-cancer agent is administered to normal tissues, side effects such as vomiting and leukocyte decrease occur. The taxane-type anti-cancer agent is administered by providing a medication cessation period in order to inhibit the side effects.

Drug Delivery Systems (DDS) exist as a means for making the taxane-type anti-cancer agent unerringly reach affected site tissues and avoiding contact between cells constituting the normal tissues and the taxane-type anti-cancer agent. As an example of the DDS, there is a technique that uses a carrier to guide drug molecules to the affected site tissues (PTL 1). However, when the carrier is used, its molecular size increases and, therefore, an administration method is limited. Furthermore, the carrier and the drug decompose before they reach the affected site tissues; and the drug which stays in the normal tissue may sometimes cause the side effects. In such a case, that will adversely affect a patient's quality of life.

The inventors of the present disclosure suggested, in PTL 2, an anti-cancer agent which does not use a carrier. PTL 2 discloses a compound in which a drug is made to bind to a metal-salen complex compound. Since the compound disclosed in PTL 2 is self-magnetic, the carrier is not required in order to carry the drug. However, there is a demand for an anti-cancer agent which has less side effects and whose cancer cell killing effect is further enhanced. Particularly, an anti-cancer agent which exhibits the excellent effect of killing cancer cells of triple-negative breast cancer has not been discovered. The anti-cancer agent which continuously kills the cancer cells is being examined from the viewpoint of enhancement of the killing effect.

CITATION LIST

Patent Literature

PTL 1: Japanese Patent Application Laid-Open (Kokai) Publication No. 2001-010978
PTL 2: Japanese Patent Application Laid-Open (Kokai) Publication No. 2012-167067

SUMMARY

Problems to be Solved by the Disclosure

It is an object of the present disclosure to provide an anti-cancer agent capable of continuously killing cancer cells. It is an object of the disclosure to provide an anti-cancer agent for killing cancer cells of breast cancer, particularly, cancer cells of triple-negative breast cancer.

Means for Solving the Problems

The present disclosure is an anticancer agent containing a complex produced by making a metal-salen complex compound, which includes a central metal and (N, N, O, O) as a quadridentate ligand and is magnetic, bind to taxane molecules which are anticancerous, and the anticancer agent is to kill cancer cells regarding which phase transition occurs between phases including Gap1, Synthesis, Gap2, and Mitosis and Cytokinesis. The present disclosure is an anti-cancer agent suited for killing cancer cells of breast cancer. Furthermore, the present disclosure is an anti-cancer agent suited for killing cancer cells of triple-negative breast cancer.

The taxane molecules included in the present disclosure should preferably be selected from either one of paclitaxel and docetaxel. The present disclosure should preferably contain the complex produced by making a metal-salen complex compound represented by either one of Formula (1) and Formula (2), bind to the taxane molecules. In Formula (1) and Formula (2), central metals $M^1$, $M^2$, and $M^3$ are independent of each other and are of any one type selected from a group consisting of Fe, Cr, Mn, Co, Ni, Mo, Ru, Rh, Pd, W, Re, Os, Ir, Pt, Nd, Sm, Eu, and Gd. The central metal of the metal-salen complex compound included in the present disclosure should preferably be Fe.

[Chem. 1]

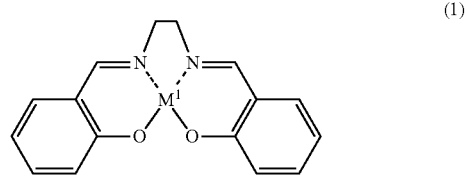

(1)

[Chem. 2]

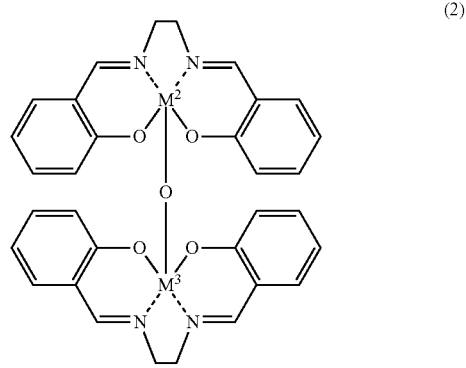

(2)

The present disclosure should preferably contain any one of complexes represented by Formula (3) or Formula (4).

[Chem. 3]

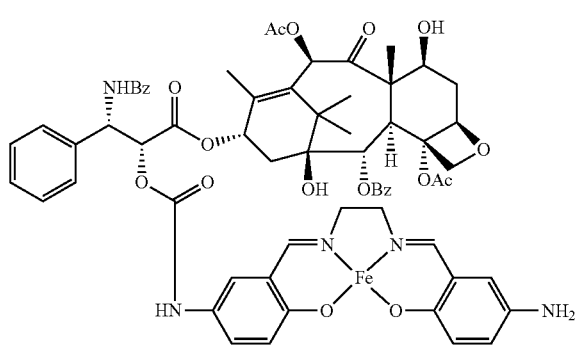

(3)

[Chem. 4]

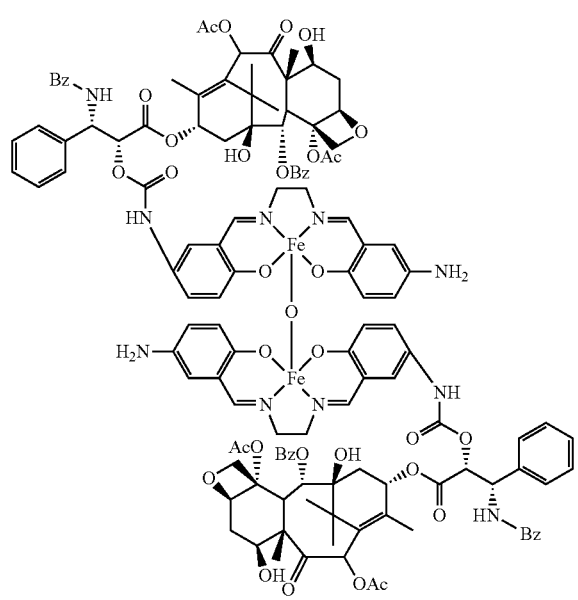

(4)

The present disclosure includes a cancer cell killing method for killing cancer cells by having an anticancer agent containing a complex produced by making a metal-salen complex compound, which includes a central metal and (N, N, O, O) as a quadridentate ligand and is magnetic, bind to taxane molecules which are anticancerous contact the cancer cells in any two or more continuous phases selected from a group consisting of Gap1, Synthesis, Gap2, and Mitosis and Cytokinesis. The cancer cell killing method of the present disclosure should preferably make the anti-cancer agent contact the cancer cells by applying an external magnetic field to affected site tissues and making the anti-cancer agent indwell in the cancer cells constituting the affected site tissues.

Advantageous Effects of Disclosure

The present disclosure can continuously kill cancer cells in a plurality of phases. Furthermore, the present disclosure can effectively kill cancer cells of breast cancer, particularly, cancer cells of triple-negative breast cancer.

DESCRIPTION OF EMBODIMENTS

[Anti-Cancer Agent]

Figure 1A:
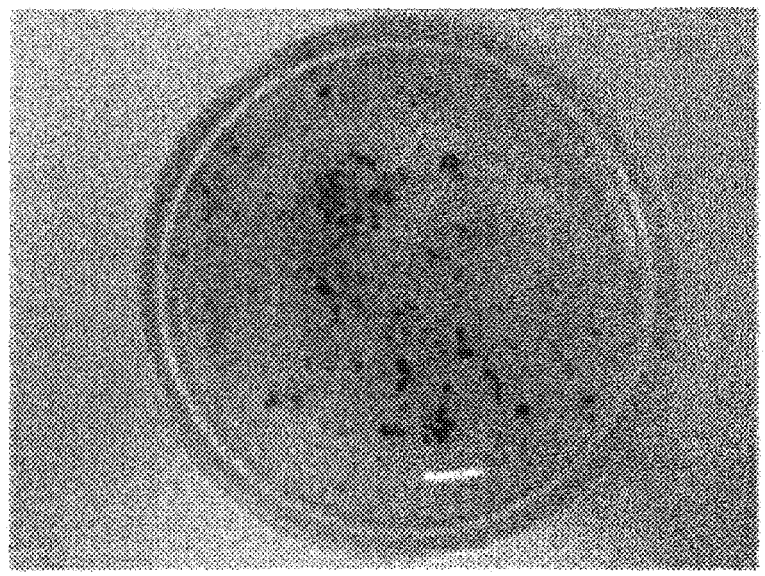
FIGS. 1A and 1B are photographs each showing results of a magnetization test of the present disclosure.

The present disclosure is an anticancer agent containing a complex produced by making a metal-salen complex compound, which includes a central metal and (N, N, O, O) as a quadridentate ligand and is magnetic, bind to taxane molecules which are anticancerous and the anticancer agent is to kill cancer cells regarding which phase transition occurs between phases including Gap1, Synthesis, Gap2, and Mitosis and Cytokinesis.

The metal-salen complex compound included in the present disclosure includes a central metal and (N, N, O, O) as a quadridentate ligand. The central metal should preferably be of any one type selected from a group consisting of Fe, Cr, Mn, Co, Ni, Mo, Ru, Rh, Pd, W, Re, Os, Ir, Pt, Nd, Sm, Eu, and Gd and, more preferably, Fe should be selected.

The metal-salen complex compound inhibits DNA replication at the G1/S phase of the cell cycle. The taxane anticancer agent inhibits cell division of the cancer cells at the G2/M phase and induces apoptosis. Therefore, the anticancer agent can be designed to kill cancer cells which make transition between phases including Gap1, Synthesis, Gap2, and Mitosis and Cytokinesis by producing a complex of the metal-salen complex compound and the taxane anticancer agent which reacts at the G2/M phase.

The metal-salen complex compound is magnetic. Therefore, when the present disclosure is made to indwell in the affected site tissues, it is possible to make the present disclosure indwell in the affected site tissues without using a carrier or the like by applying a magnetic field to the affected site tissues. As the carrier is not used, the present disclosure can reduce the molecular size and provide the anti-cancer agent which can be orally administered. The magnetic property of the present disclosure that uses the metal-salen complex compound which is represented by Formula (1) and whose central metal $M^1$ is Fe can be measured by using a known magnetic property measurement device. An example of the known magnetic property measurement device can include MPMS3 (SQUID) manufactured by Quantum Design, Inc. in the U.S. According to measurement results, magnetization of the metal-salen complex compound represented by Formula (1) increases proportionally with respect to the application of the magnetic field. Therefore, the present disclosure can be delivered to the affected site tissues by using the external magnetic field.

Furthermore, as a result of such application, the temperature of the anti-cancer agent itself increases to a temperature at which it can kill the cancer cells. Accordingly, more cancer cells can be killed by the heat of the anti-cancer agent by making the anti-cancer agent of the present disclosure contact the cancer cells. Specifically speaking, cells which are already in the S phase are most effectively killed. For example, regarding the present disclosure including an Fe-salen complex compound which is ferromagnetic, when the magnetic field is applied, the temperature of the present disclosure rises by 2 to 20° C. Specifically speaking, when the present disclosure is made to indwell in the affected site tissues to which the magnetic field is applied at room temperature, the temperature of the present disclosure becomes approximately 37 to 60° C. and then 40 to 60° C. The cancer cells are killed under temperature condition of 38 to 50° C. Specifically speaking, the temperature of the present disclosure after the application of the magnetic field exceeds the cancer cell killing temperature. Therefore, the cancer cells can be killed more effectively by making the anti-cancer agent of the present disclosure contact the cancer cells.

The metal-salen complex compound should preferably be a metal-salen complex compound represented by Formula (1). In Formula (1), the central metal $M^1$ is any one type selected from a group consisting of Fe, Cr, Mn, Co, Ni, Mo, Ru, Rh, Pd, W, Re, Os, Ir, Pt, Nd, Sm, Eu, and Gd.

[Chem. 1]

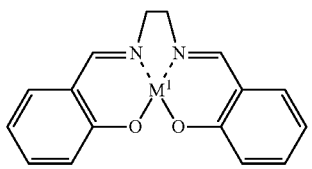

(1)

Furthermore, the metal-salen complex compound should also preferably be a metal-salen complex compound represented by Formula (2). In Formula (2), a central metal $M^2$ and a central metal $M^3$ are independent of each other and are of any one type selected from a group consisting of Fe, Cr, Mn, Co, Ni, Mo, Ru, Rh, Pd, W, Re, Os, Ir, Pt, Nd, Sm, Eu, and Gd. The central metal $M^2$ and the central metal $M^3$ may be the same or different from each other.

[Chem. 2]

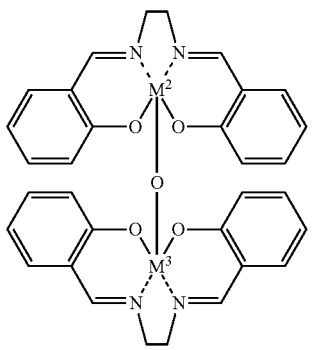

(2)

The present disclosure that uses a metal-salen complex compound which is represented by Formula (2) and in which both the central metal $M^2$ and the central metal $M^3$ are Fe is a ferromagnetic substance according to its hysteresis loop. When the same central metal is used for $M^1$, $M^2$, and $M^3$, the magnetic property of the present disclosure which uses the metal-salen complex compound represented by Formula (2) tends to become higher than that of the present disclosure which uses the metal-salen complex compound represented by Formula (1).

Examples of the taxane molecules which are included in the present disclosure and which are anticancerous are paclitaxel and docetaxel. These taxane molecules have cell-division-inhibiting effect on cancer cells in the G2 phase and the M phase. The paclitaxel and docetaxel particularly exhibit the cell-division-inhibiting effect, as antimicrotubule agents, on the cancer cells of, for example, breast cancer, non-small cell lung cancer, gastric cancer, head and neck cancer, and ovarian cancer.

The present disclosure contains a complex produced by making a specified metal-salen complex compound bind to taxane molecules. Accordingly, cancer cells regarding which phase transition occurs between phases including Gap1, Synthesis, Gap2, and Mitosis and Cytokinesis can be killed. Specifically speaking, the present disclosure also exhibits the killing effect on the cancer cells in any phase of the G1 phase, the S phase, the G2 phase, and the M phase. Therefore, the present disclosure can kill the can cells in any continuous phases from the G1 phase to the M phase. Since the present disclosure is magnetic, the present disclosure can indwell intensively in the affected site tissues and continuously inhibit cell division of the cancer cells. During the phase transition from the G1 phase to the M phase, the present disclosure should preferably be made to always dwell in the affected site tissues and kill the cancer cells. Furthermore, since the anti-cancer agent is prevented from contacting normal tissue cells, it is possible to inhibit the side effects.

In recent years, there is a demand for further improvements of therapeutic effects by a triple-negative breast cancer treatment using paclitaxel and docetaxel. The operation and effect of the present disclosure is also exhibited on cancer cells of the triple-negative breast cancer as explained in Examples later.

The complex of the metal-salen complex compound and the taxane molecules can be manufactured by causing a metal-salen complex compound, which is manufactured by a conventional known method, and the taxane molecules to react and crystallize in an organic solvent. Detailed specific examples will be described in Examples.

An anti-cancer agent containing a monomer Fe-salen complex and paclitaxel can be listed as a specific example of the present disclosure. The complex can be represented by Formula (3).

[Chem. 3]

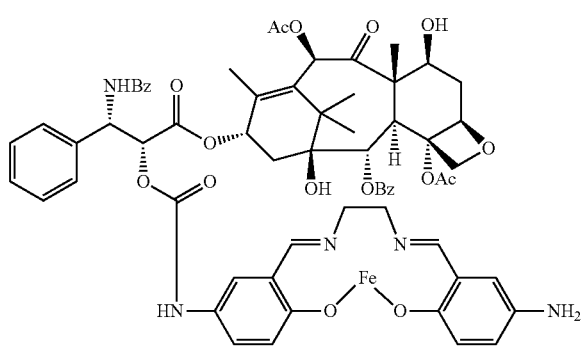

(3)

An anti-cancer agent containing a dimer Fe-salen complex and paclitaxel can be listed as another specific example. The complex can be represented by Formula (4).

[Chem. 4]

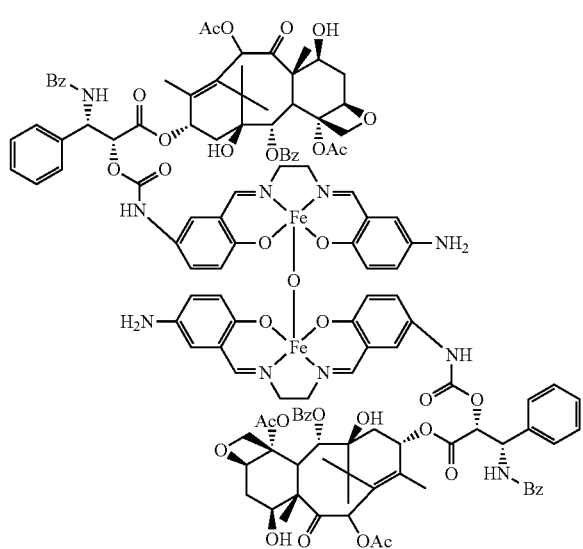

(4)

[Cancer Cell Killing Method]

A cancer cell killing method according to the present disclosure is a cancer cell killing method for killing cancer cells by having an anticancer agent containing a complex produced by making a metal-salen complex compound, which includes a central metal and (N, N, O, O) as a quadridentate ligand and is magnetic, bind to taxane molecules which are anticancerous contact the cancer cells in any two or more continuous phases selected from a group consisting of Gap1 (G1 phase), Synthesis (S phase), Gap2 (G2 phase), and Mitosis and Cytokinesis (M phase). According to the above-described present disclosure, the anti-cancer agent should preferably be made to contact the cancer cells by applying an external magnetic field to affected site tissues and making the anti-cancer agent indwell in the cancer cells constituting the affected site tissues.

According to the present disclosure, an anti-cancer agent which also exhibits the effect of killing cancer cells in any phase of the G1 phase, the S phase, the G2 phase, and the M phase is used. The present disclosure can kill the cancer cells in any continuous phases from the G1 phase to the M phase by making such anti-cancer agent contact the cancer cells. Furthermore, since the anti-cancer agent is magnetic, it can be guided precisely to the affected site tissues and made to indwell there. Therefore, the cancer cells can be killed by a minimum required amount of the anti-cancer agent. Furthermore, since the anti-cancer agent can be prevented from indwelling in the normal tissues, it is possible to inhibit the side effects.

The present disclosure is suited as a cancer killing method for cancer such as breast cancer, non-small cell lung cancer, gastric cancer, head and neck cancer, and ovarian cancer. Particularly, it is an effective method as a cancer cell killing method for triple-negative breast cancer.

EXAMPLES

The present disclosure will be explained by using Examples. However, the present disclosure is not limited to the following Examples.

Example 1

[Anti-Cancer Agent Synthesis Method 1]

A method for synthesizing the complex produced by making the Fe-salen complex compound bind to paclitaxel will be explained as a first synthesis method of the anti-cancer agent of the present disclosure. By the synthesis method 1, firstly acetic anhydride and $H_2SO_4$ were added to Compound 1 under condition of room temperature (25 to 27° C.) and mixed until they were uniformly dispersed. Mixing time was one hour. A reaction was caused by using a Thin-Layer Chromatography (TLC). After the reaction ended, the obtained product was recrystallized by using ethyl acetate/phosphatidyl ethanolamine (P.E.), thereby obtaining Compound 2. Compound 2 was identified by means of mass spectrometry.

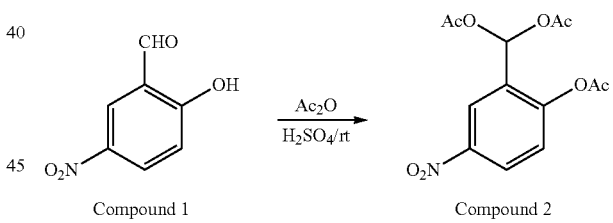

Compound 1       Compound 2

Compound 2 and carbons containing palladium (10%) were added to methanol and a hydrogenation treatment was conducted in a hydrogen atmosphere. After the hydrogenation treatment, the obtained compound was filtered, thereby obtaining Compound 3. Compound 3 was identified by means of the mass spectrometry.

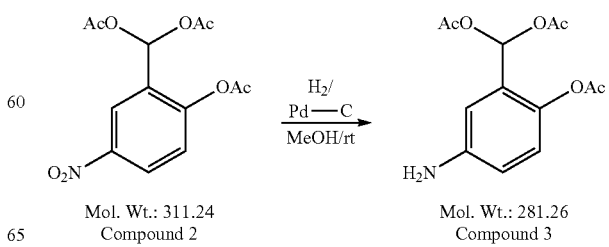

Mol. Wt.: 311.24       Mol. Wt.: 281.26
Compound 2             Compound 3

A solution in which Compound 3 and di(tert-butyl) decarbonate were added to dichloromethane (DCM) was obtained. The solution was stirred overnight, a solvent of the solution was allowed to evaporate in vacuum, and Compound 3 and di(tert-butyl) dicarbonate were caused to react. Oil attached to the obtained reaction product was cleaned with methanol and a solution was obtained by adding an aqueous NaOH solution. After refluxing the solution for 5 hours, the solution was refined by flash chromatography using silica gel, thereby obtaining Compound 5.

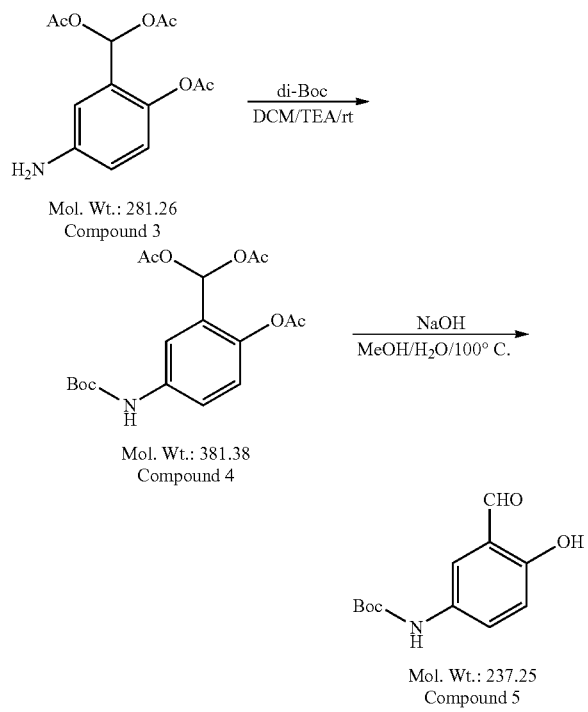

A solution was obtained by dissolving Compound 5 in ethanol. A few drops of ethylenediamine were added to the solution and refluxing was started in a hot bath. The reflux was completed when 0.5 hours elapsed after the start of the reflux. The solution was filtered, thereby obtaining Compound 6. An optical microscope was used to check Compound 6 and it was found that Compound 6 was a ligand with faint yellow needle-like Shiff bases.

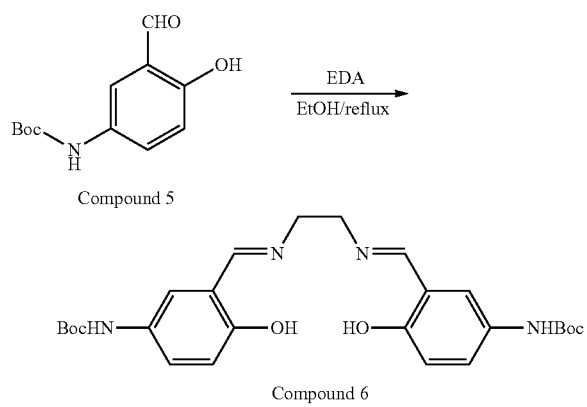

A solution was obtained by adding ether and hydrochloric acid to Compound 6 in DCM. The solution was stirred at room temperature for 5 hours. Then, the solution was filtered and cleaned by using DCM and ether, thereby obtaining Compound 7. Compound 7 was identified by using $^1$HNMR.

A few drops of 4-nitrophenyl chloroformate which was dissolved in DCM were added to paclitaxel which was dissolved in DCM. After the solution in which paclitaxel and 4-nitrophenyl chloroformate were dissolved in DCM was stirred at −50° C. for 3 hours, the solvent was removed. After the solvent was removed, the obtained solid product was refined by means of flash chromatography using silica gel, thereby obtaining Compound 8. Compound 8 was identified by means of the mass spectrometry. Its yield was 68%.

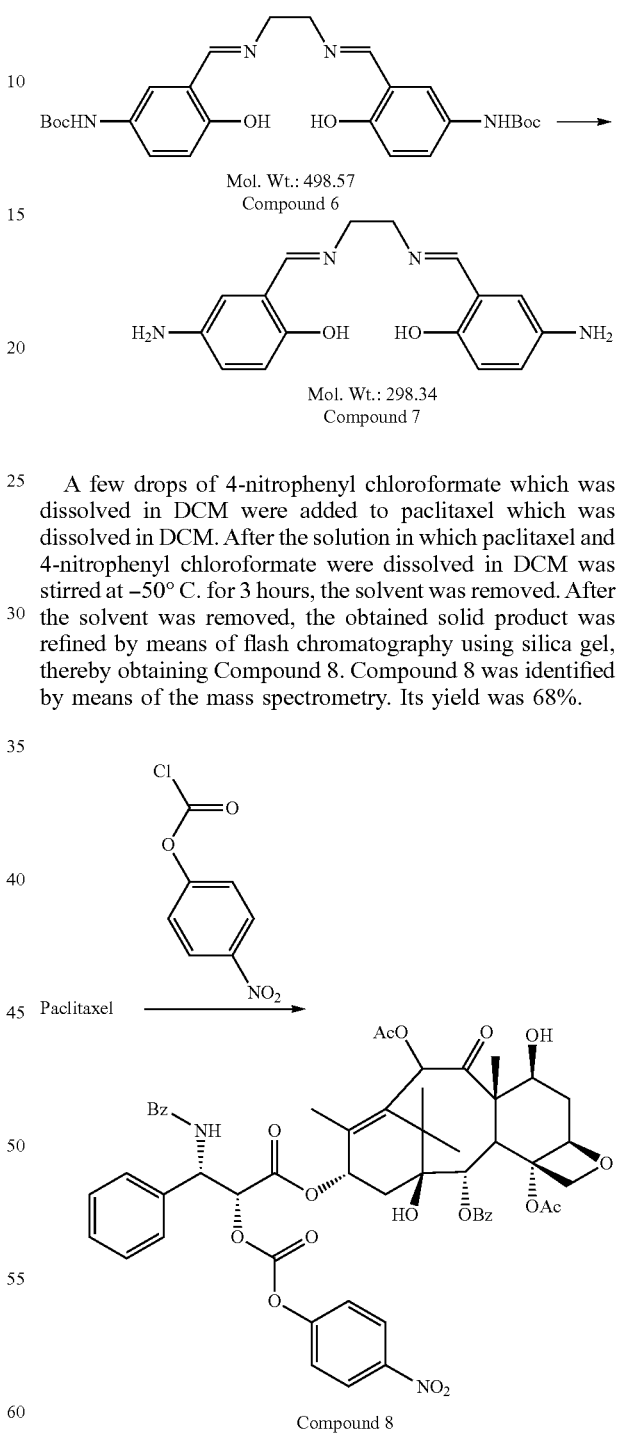

Compound 8 (246 mg (0.24 mmol)) and $K_2CO_3$ (99 mg (0.72 mmol)) were added to anhydrous N,N-dimethylformamide (DMF). Furthermore, Compound 7 (−30° C. and 144 mg (0.48 mmol)) was dissolved in anhydrous DMF. The solution containing Compound 7 was dripped into the solution containing Compound 8 in a nitrogen atmosphere and the obtained mixed solution was stirred at −20° C. for 3 hours. After filtering the mixed solution, the obtained crude product was treated with 30 ml of ethanol/diethyl ether (1:1).

The crude product after the treatment was dissolved in 5 ml of methanol and 43 mg (0.22 mmol) of $FeCl_2.4H_2O$ was further added to it in a nitrogen atmosphere. The obtained dark brown product was stirred at 40° C. in the nitrogen atmosphere for 30 minutes. After the stirring was finished, the solvent was removed in vacuum. Methanol and diethyl ether were added to the residual solid and the obtained mixture was recrystallized. The solvent was removed in vacuum and 130 mg of Compound 9 was recovered. As a result of mass spectrometry of Compound 9, it was confirmed that Compound 9 was a complex of the Fe-salen complex and paclitaxel. The yield of Compound 9 was 48%. The mass spectrometry was conducted by the API-ES method. Regarding measurement results, a calculated value was 1272.40 and an actual measurement value was 1272.00.

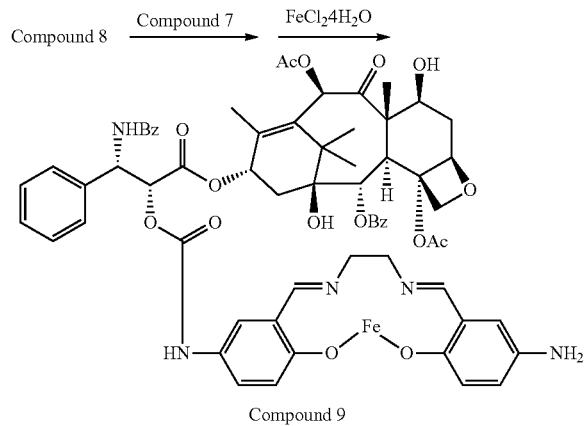

Example 2

[Anti-Cancer Agent Synthesis Method 2]

A method for synthesizing a complex produced by making a dimer Fe-salen complex compound bind to paclitaxel will be explained as a second synthesis method of the anti-cancer agent according to the present disclosure. Steps of the synthesis method 2 from the start to the steps of obtaining Compound 7 and Compound 8 are the same as those of the synthesis method 1. $FeCl_3$, instead of $FeCl_2.4H_2O$, was added to the crude product recovered from the mixed solution containing Compound 7 and Compound 8 and chelates of the metal-salen complex compound were generated. The obtained solid substance was recrystallized and the solvent was removed, thereby obtaining Compound 9. Mass spectrometry of Compound 9 was performed and it was confirmed that Compound 9 was the complex of the dimer Fe-salen complex compound and paclitaxel. The mass spectrometry was conducted by the API-ES method. Regarding measurement results, a calculated value was 2478.74 and an actual measurement value was 2481.60.

Example 3

[Magnetic Property of Anti-Cancer Agent]

Figure 1B:
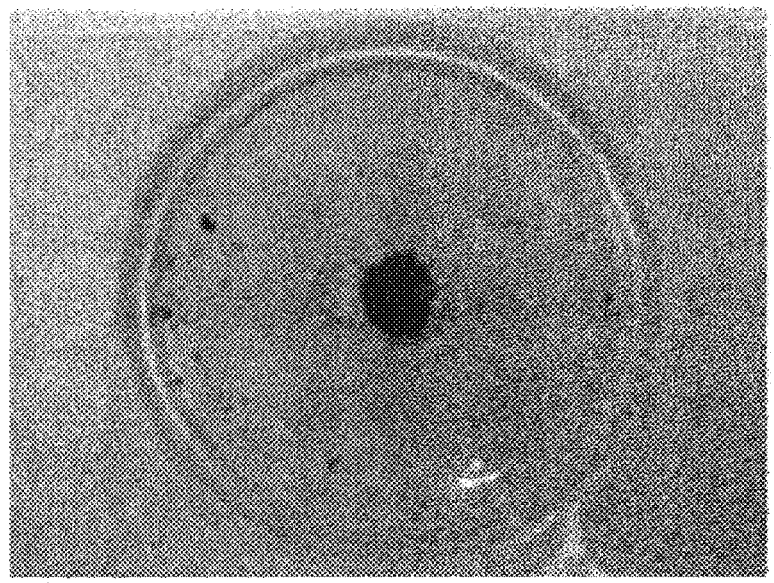

The complex obtained in Example 1 by making the monomer iron-salen complex bind to paclitaxel and the complex obtained in Example 2 by making the dimer iron-salen complex bind to paclitaxel were added as appropriate to purified water in a round Petri dish and a neodymium permanent magnet (surface magnetic flux density: 800 mT) was placed closer to the bottom of the round Petri dish and the status of each complex in the purified water was observed. FIG. 1A shows a photograph of the status of the above-mentioned two types of complexes in the round Petri dish in a state where the magnet is not placed close to the Petri dish. FIG. 1B shows a photograph of the status of the above-mentioned two types of complexes in the round Petri dish in a state where the magnet is placed close to the Petri dish. As a result of comparing photographs of FIG. 1A and FIG. 1B, both the two types of complexes were dispersed in the purified water in the state where the magnet is not placed close to the Petri dish. On the other hand, when the magnet is placed close to the Petri dish, both the two types of complexes gathered to an area to which the magnetic field is applied. Accordingly, it was confirmed that the complex(es) produced by making the iron-salen complex bind to paclitaxel was magnetic.

Example 4

[Cancer Cell Killing Effect Assay 1]

An assay to check the cancer cell killing effect of the complex obtained in Example 1 by making the monomer iron-salen complex bind to paclitaxel (hereinafter referred to as "Example 1") was performed. An assay method will be described below.

1. Cancer Cell Line: Cancer Cell Line (MCF-7) (G0/G1 Phase: 80%) for Breast Cancer The above-mentioned MCF-7 was assigned by RIKEN.

2. Assay Reagent

A 2,3,-bis(2-methoxy-4-nitro-5-sulfophenyl)-5-[(phenylamino)-carbonyl]-2H-tetrazolium inner salt (XTT) cell proliferation assay kit (XTT cell proliferation assay kit) manufactured by American Type Culture Collection (ATCC) was used. An XTT labeled liquid mixture was adjusted by mixing an XTT reagent (5 ml) and an activation solution (0.1 ml).

3. Assay Method

The cell proliferation assay was conducted in accordance with ATCC's experiment protocol. Regarding the details of the XTT assay, reference was made to Reference 1 published by the inventors of the present disclosure.

REFERENCE 1

Sato I, Umemura M, Mitsudo K, Kioi M, Nakashima H, Iwai T, Feng X, Oda K, Miyajima A, Makino A, Iwai M, Fujita T, Yokoyama U, Okumura S, Sato M, Eguchi H, Tohnai I, Ishikawa Y., Hyperthermia generated with ferucarbotran (Resovist(R)) in an alternating magnetic field enhances cisplatin-induced apoptosis of cultured human oral cancer cells. J Physiol Sci, 64 (2014) 177-183.

(1) Cell Proliferation

RPMI-1640 (Wako, Osaka) was added, as a culture medium, to each well (100 μl) of a microplate (for cell proliferation and with 96 holes and a flat bottom). Furthermore, 10% inactivated bovine serum (GIBCO, USA) and 100 units/ml of penicillin-streptomycin (Wako, Osaka) were added. The cancer cell line (MCF-7) for breast cancer was seeded in the culture medium and was cultured under condition of 37° C. and 5% $CO_2$.

(2) XTT Assay

The aqueous solution of Example 1 was adjusted to concentrations of 1.875 µM, 3.750 µM, 7.500 µM, 15.00 µM, 30.00 µM, and 60.00 µM. RPMI-1640, 10% inactivated bovine serum (GIBCO, USA), and 100 units/ml of penicillin-streptomycin were added to each well (100 µl) of the microplate (for cell proliferation and with 96 holes and a flat bottom) and $3 \times 10^5$ cultured cells were seeded. Furthermore, the aqueous solution adjusted to each concentration was added to each well and was cultured for 24 hours under condition of 37° C. and 5% $CO_2$.

Figure 2:
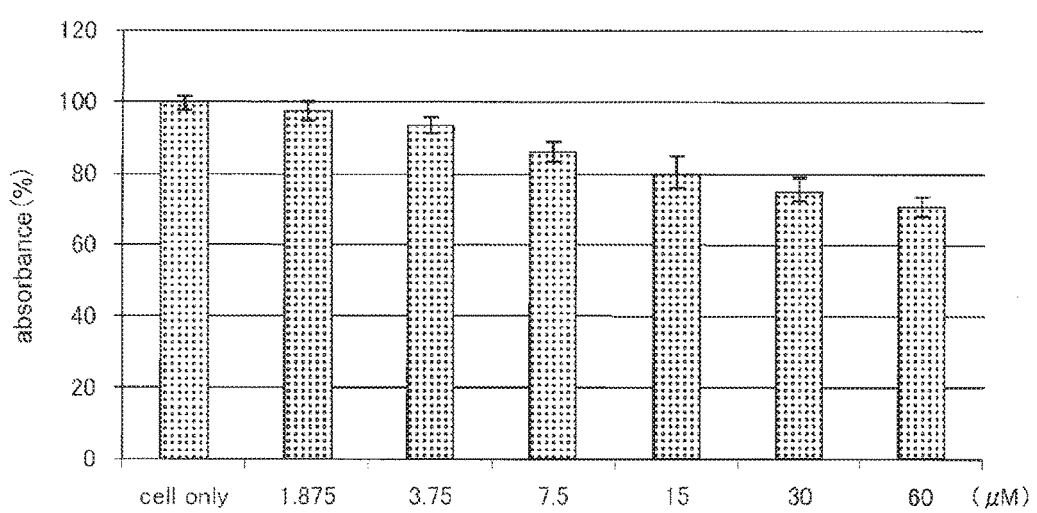
FIG. 2 is a diagram illustrating results of an XTT assay of cancer cells which an example of the present disclosure was made to contact.

The culture medium of each well was replaced and the XTT labeled liquid mixture was added and culturing was performed under condition of 37° C. and 5% $CO_2$. After the culture medium was removed, a solvent was added to dissolve formazan dye and absorbance measurement at 450 nm was performed. The absorbance measurement was performed by using a Model 680 microplate Reader (manufactured by BIO-RAD Laboratories, CA, USA). A reference wavelength was set at 665 nm. Measurement results are shown in FIG. 2.

Example 5, Comparative Example 1, Comparative Example 2

[Cancer Cell Killing Effect Assay 2]

Example 1 and Taxol (registered trademark) were adjusted with physiological saline so that each of them would become 30.00 µM.

Figure 3:
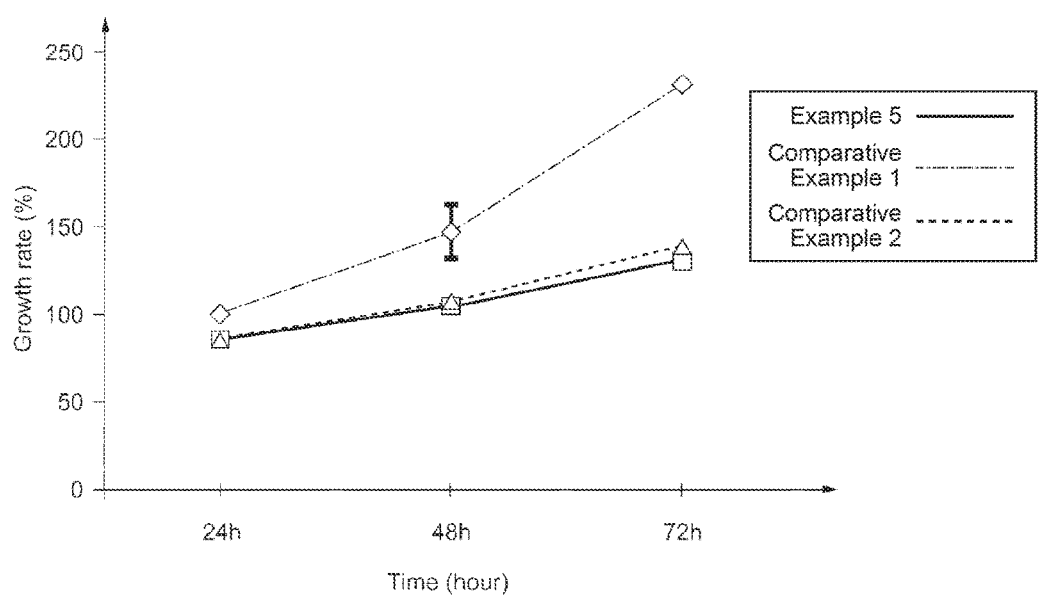
FIG. 3 is a diagram illustrating an example of a cell growth rate of the cancer cells which the present disclosure was made to contact.

The cancer cell line (MCF-7) for breast cancer was cultured by the same culturing method as that of Example 4. A proliferation example obtained by adding the solution of Example 1 to each well of the microplate was used as Example 5. A proliferation example obtained by not adding either the solution of Example 1 or the Taxol solution to the culture medium was used as Comparative Example 1. A proliferation example obtained by adding the Taxol solution was used as Comparative Example 2. The number of living cells 24 hours, 48 hours, and 72 hours after the start of culturing was counted. The number of living cells was calculated on the basis of absorbance by performing the XTT assay in the same manner as in Example 4. A cell growth rate was calculated and shown in FIG. 3.

Examples 6-10, Comparative Examples 3-6

The solution of Example 1 and a commercially available paclitaxel solution were adjusted to concentrations indicated in Table 1 and the obtained solutions were used as Examples 6-10 and Comparative Examples 4-6. A case in which neither Example 1 nor paclitaxel was added was Comparative Example 3.

TABLE 1

|  |  | Concentration (µM) |
|---|---|---|
| Example 1 | Example 6 | 3.750 |
|  | Example 7 | 5.000 |
|  | Example 8 | 7.500 |
|  | Example 9 | 15.00 |
|  | Example 10 | 30.00 |
| No Additives | Comparative Example 3 | 0.000 |
| paclitaxel | Comparative Example 4 | 3.750 |
|  | Comparative Example 5 | 5.000 |
|  | Comparative Example 6 | 7.500 |

[Cancer Cell Killing Effect Assay 3]

The killing effect assay was performed on the cancer cells of Example 1.
1. Cancer Cell Line: Cancer Cell Line (MDA-MB-453) (G0/G1 Phase: 80%) for Breast Cancer The above-mentioned cancer cell line for the triple-negative breast cancer was assigned by RIKEN.
2. XTT Assay:

The XTT cell proliferation assay kit (manufactured by ATCC) was used. The XTT labeled liquid mixture was adjusted by mixing the XTT reagent (5 ml) and an activation solution (0.1 ml).
3. Assay Method The cell proliferation assay was conducted in accordance with ATCC's experiment protocol. Furthermore, regarding the details of the XTT assay, reference was made to Reference 1 mentioned earlier.

The cancer cell line for the triple-negative breast cancer was cultured by the same method as that of Example 4. RPMI-1640, 10% inactivated bovine serum (GIBCO, USA), and 100 units/ml of penicillin-streptomycin were added to each well (100 µl) of the microplate (for cell proliferation and with 96 holes and a flat bottom) and $3 \times 10^5$ cultured cells were seeded. Furthermore, each of Example 6, Example 8, Comparative 4, and Comparative 6 was added to each well and culturing was performed for 24 hours under condition of 37° C. and 5% $CO_2$. Furthermore, culturing without adding either solution of the present disclosure or paclitaxel was also performed under the same condition (Comparative Example 3).

The XTT assay was performed by the same method as that of Example 4. A cell survival rate was calculated on the basis of the manufacturer's protocol of the XTT Cell Proliferation Assay Kit (by ATCC).

Figure 4:
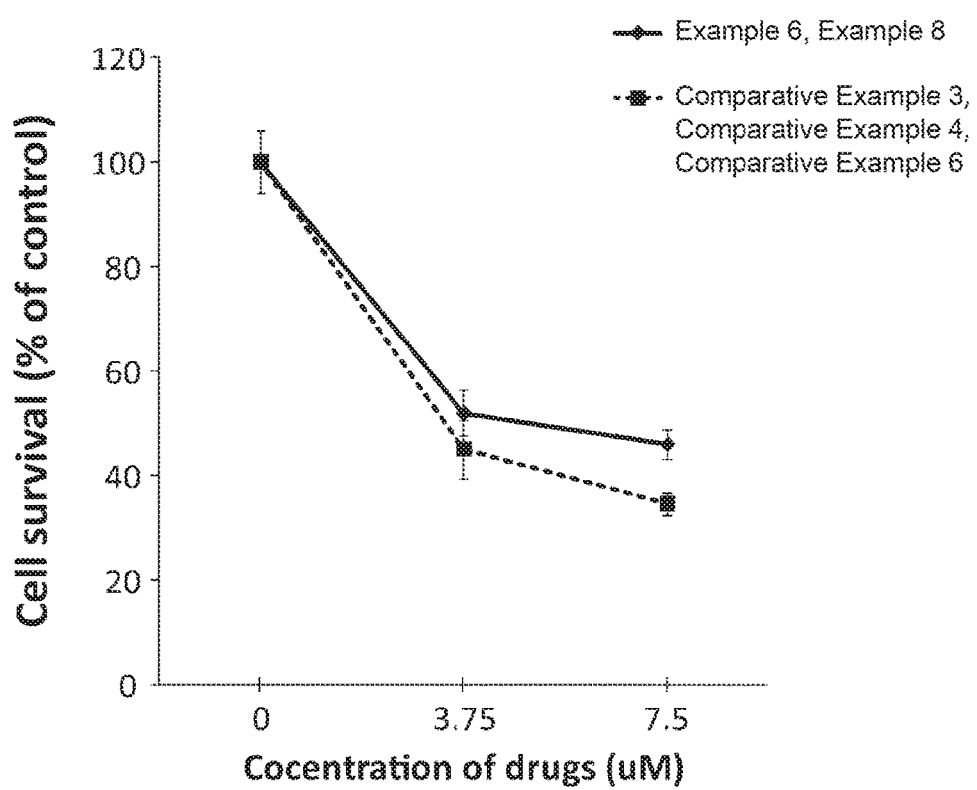
FIG. 4 is a diagram illustrating an example of the cell survival rate of the cancer cells which the present disclosure was made to contact.

As shown in FIG. 4, the cell survival rate was lower in the wells where the solution of each Example was added and cultivated than that of the wells where the solution of each Example was not added. Furthermore, the cell survival rate of the solution of the concentration 7.500% was lower than that of 3.750%. As a result, it was confirmed that the cell killing effect of the present disclosure is concentration-dependent. Since the present disclosure has the magnetic property, it can be easily guided to the affected site region. Accordingly, a high concentration of the magnetic medicinal drug of the present disclosure can be made to indwell in the affected site region. Therefore, the present disclosure exhibits the excellent cell killing effect.

[Cancer Cell Killing Effect Assay 4]

A cancer cell killing effect assay by the heat effect of Example 1 was performed.
1. Cancer Cell Line: Cancer Cell Line (MDA-MB-453) (G0/G1 Phase: 80%) for Breast Cancer The above-mentioned cancer cell line for the triple-negative breast cancer was assigned by RIKEN.
2. XTT Assay:

The XTT cell proliferation assay kit (manufactured by ATCC) was used. The XTT labeled liquid mixture was adjusted by mixing the XTT reagent (5 ml) and an activation solution (0.1 ml).
3. Assay Method The cell proliferation assay was conducted in accordance with ATCC's experiment protocol. Furthermore, regarding the details of the XTT assay, reference was made to Reference 1 mentioned earlier.
(1) Cell Proliferation The cancer cell line for the triple-negative breast cancer was cultured by the same method as that of Example 4. RPMI-1640, 10% inactivated bovine serum (GIBCO, USA), and 100 units/ml of penicillin-streptomycin were added to each well (100 µl) of the microplate (for cell proliferation and with 96 holes and a flat bottom) and $3 \times 10^5$ cultured cells were seeded. Furthermore, each of Example 6, Example 8, Example 9, and Example 10 was added to each well and culturing was performed for 24 hours under condition of 25° C. and 5% $CO_2$. Furthermore, regarding other wells, a magnetic field was applied to the wells, the temperature of Example 6, Example 8, Example 9, and Example 10 was set to 50° C., and culturing was performed for 24 hours under the condition of 5% $CO_2$. Furthermore, culturing without adding either aqueous solution of the present disclosure or paclitaxel was also performed at room temperature and at 50° C. in the same manner (Comparative Example 3).

The XTT assay was performed by the same method as that of Example 4. The cell survival rate was calculated on the basis of the results of the absorbance measurement and by the method explained in [Cancer Cell Killing Effect Assay 3]. The cell survival rate is shown in FIG. 5.

Figure 5:
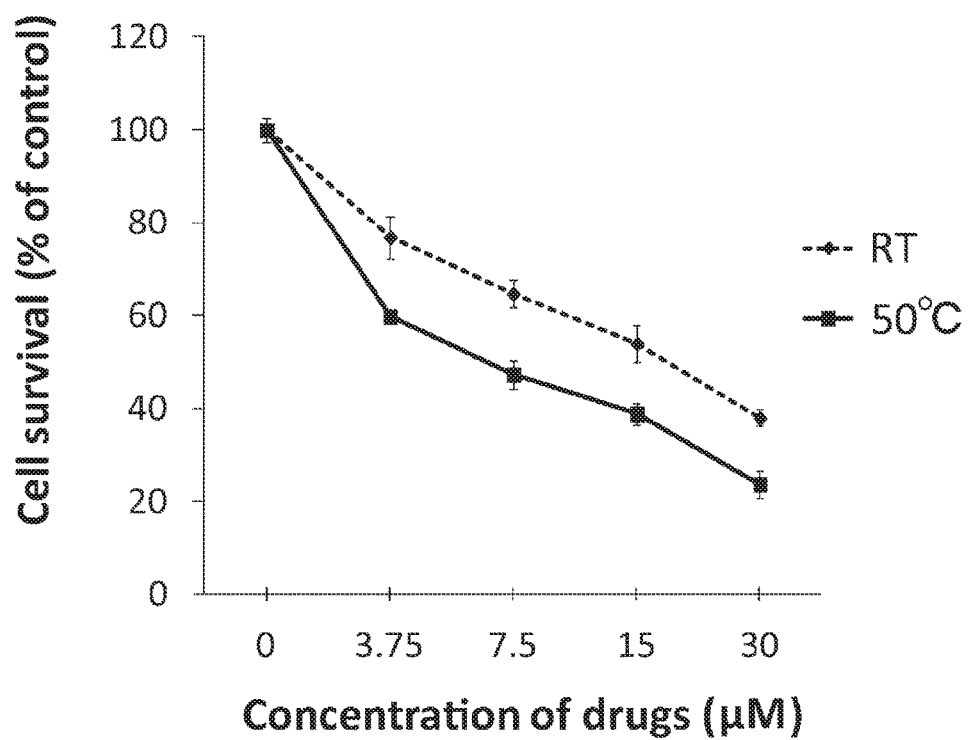
FIG. 5 is a diagram illustrating an example of the cell survival rate of the cancer cells which the present disclosure was made to contact.

As shown in FIG. 5, it was confirmed that the cancer cell killing effect of the present disclosure is enhanced, by applying the magnetic field, more than the case where the present disclosure is used at room temperature. Specifically speaking, the cancer cell killing effect promoted by the heat effect according to the present disclosure was confirmed.

[Cancer Cell Killing Effect Assay 5]

The killing effect assay was performed on the cancer cells of Example 1.

1. Cancer Cell Line: Cancer Cell Line (MDA-MB-231) (the G0 Phase) for Triple-Negative Breast Cancer The above-mentioned cancer cell line for the triple-negative breast cancer was assigned by RIKEN.

2. XTT Assay:

XTT cell proliferation assay kit (manufactured by ATCC) The XTT labeled liquid mixture was adjusted by mixing the XTT reagent (5 ml) and an activation solution (0.1 ml).

3. Assay Method

The cell proliferation assay was conducted in accordance with ATCC's experiment protocol. Furthermore, regarding the details of the XTT assay, reference was made to Reference 1 mentioned earlier.

The cancer cell line for the triple-negative breast cancer was cultured by the same method as that of Example 4. RPMI-1640, 10% inactivated bovine serum (GIBCO, USA), and 100 units/ml of penicillin-streptomycin were added to each well (100 μl) of the microplate (for cell proliferation and with 96 holes and a flat bottom) and $3\times10^5$ cultured cells were seeded. Furthermore, each of Example 6, Example 8, Comparative Example 4, and Comparative Example 6 was added to each well and culturing was performed for 24 hours under condition of 37° C. and 5% $CO_2$. Furthermore, culturing without adding either solution of the present disclosure or paclitaxel was also performed under the same condition (Comparative Example 3).

Figure 6:
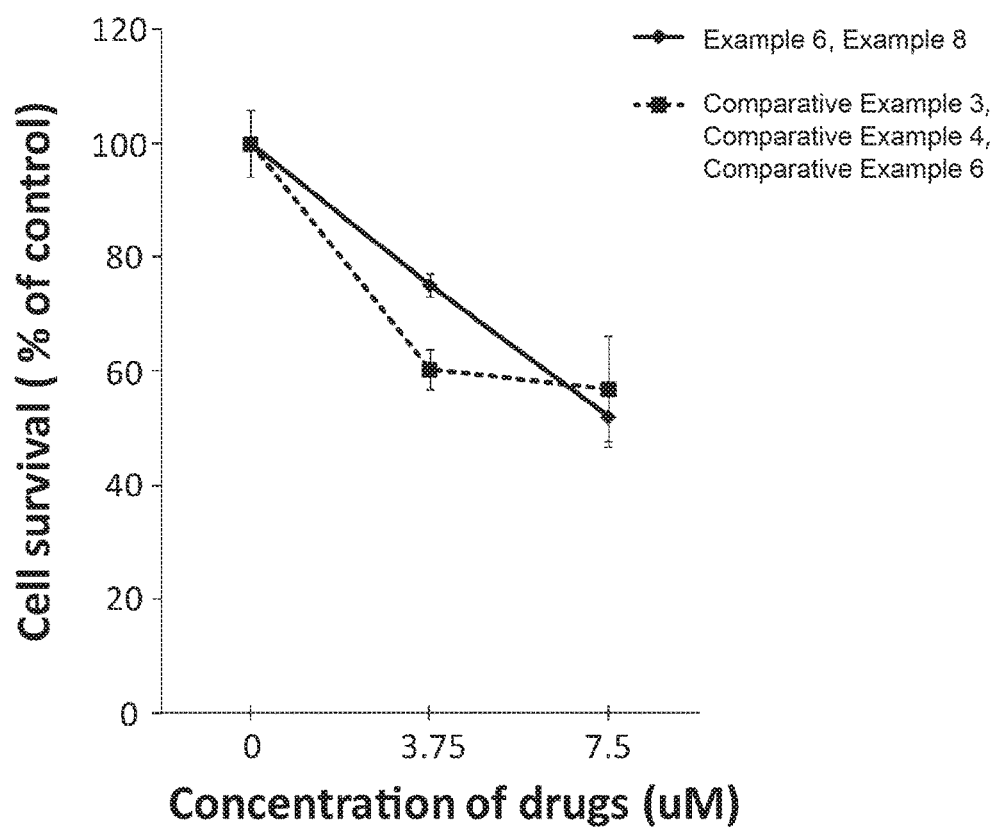
FIG. 6 is a diagram illustrating an example of the cancer cells which the present disclosure was made to contact.

The XTT assay was performed by the same method as that of Example 4. The cell survival rate was calculated on the basis of the results of the absorbance measurement and by the method explained in [Cancer Cell Killing Effect Assay 3]. FIG. 6 shows the cell survival rates of Example 6, Example 8, Comparative Example 4, and Comparative Example 6.

As shown in FIG. 6, a reduction of the cell survival rate when using the commercially available paclitaxel was concentration-dependent up to a specified concentration; however, when the concentration exceeds a certain value, the improvement of the cell killing effect slowed down. On the other hand, the cell killing effect of the present disclosure is concentration-dependent. Therefore, even if one dosage is relatively large, the present disclosure can be made to indwell precisely in the affected site tissues and can thereby continue its cell killing effect.

[Cancer Cell Killing Effect Assay 6]

The killing effect check assay was performed on the cancer cells of Example 1.

1. Cancer Cell Line: Cancer Cell Line (MDA-MB-453) for Triple-Negative Breast Cancer The above-mentioned cancer cell line for the triple-negative breast cancer was assigned by RIKEN.

2. XTT Assay

XTT cell proliferation assay kit (manufactured by American Type Culture Collection) The XTT labeled liquid mixture was adjusted by mixing the XTT reagent (5 ml) and an activation solution (0.1 ml).

3. Assay Method

The cell proliferation assay was conducted in accordance with ATCC's experiment protocol. Furthermore, regarding the details of the XTT assay, reference was made to Reference 1 mentioned earlier.

The cancer cell line for the G0 phase of the triple-negative breast cancer was cultured by the same method as that of Example 4. RPMI-1640, 10% inactivated bovine serum (GIBCO, USA), and 100 units/ml of penicillin-streptomycin were added to each well (100 μl) of the microplate (for cell proliferation and with 96 holes and a flat bottom) and $3\times10^5$ cultured cells were seeded. Furthermore, Example 7 was added to each well and cultured for 24 hours under the condition of 37° C. and 5% $CO_2$. Furthermore, culturing without adding either solution of the present disclosure or paclitaxel was also performed under the same condition (Comparative Example 3).

The number of cells in the G1 phase, the S phase, and the M phase was counted according to the experiment protocol of the XTT cell proliferation assay kit (manufactured by ATCC) or by the method disclosed in Reference 1 mentioned earlier.

Figure 7:
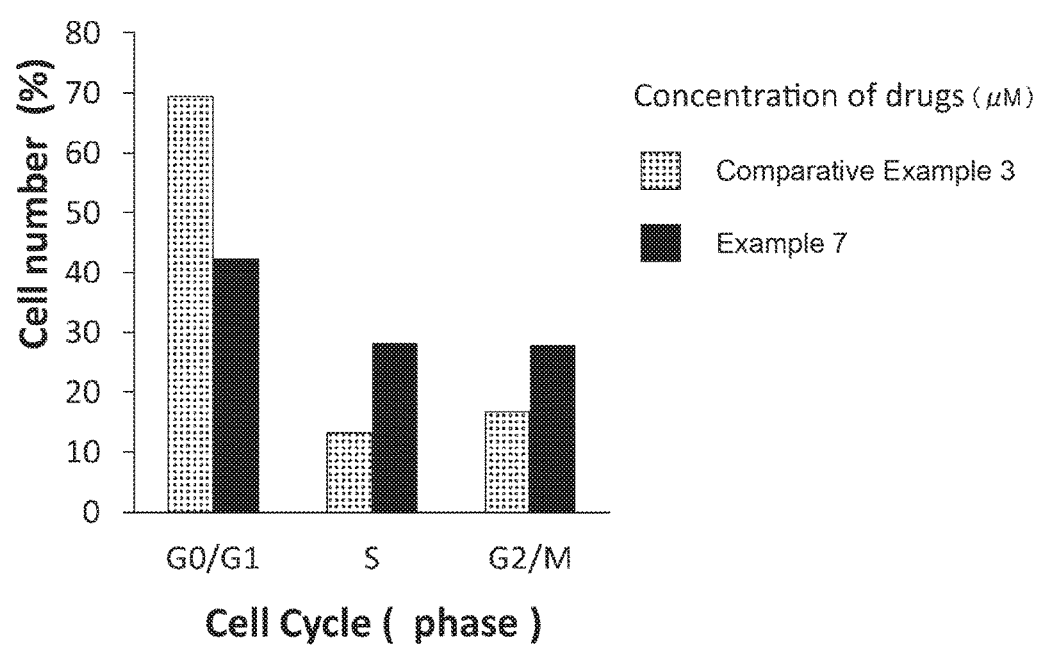
FIG. 7 is a diagram illustrating an example of a cell cycle rate of the cancer cells which the present disclosure was made to contact.

The number of living cells was counted according to the XTT assay by the same method as that of Example 4. The cell survival rate was calculated on the basis of the results of the absorbance measurement and by the method explained in [Cancer Cell Killing Effect Assay 3]. FIG. 7 shows cell cycle rates of Example 7 and Comparative Example 3, which were measured with a flow cytometer.

[Cancer Cell Killing Effect Assay 7]

1. Cancer Cell Line: Cancer Cell Line (MDA-MB-453) for Triple-Negative Breast Cancer The above-mentioned MDA-MB-453 was assigned by RIKEN.

2. XTT Assay:

The XTT cell proliferation assay kit (manufactured by ATCC) was used.

The XTT labeled liquid mixture was adjusted by mixing the XTT reagent (5 ml) and an activation solution (0.1 ml).

3. Assay Method

The cell proliferation assay was conducted in accordance with ATCC's experiment protocol. Regarding the details of the XTT assay, reference was made to Reference 1 mentioned earlier.

The cancer cell line for the G2 phase of the triple-negative breast cancer was cultured by the same method as that of Example 4. RPMI-1640, 10% inactivated bovine serum (GIBCO, USA), and 100 units/ml of penicillin-streptomycin were added to each well (100 μl) of the microplate (for cell proliferation and with 96 holes and a flat bottom) and $3\times10^5$ cultured cells were seeded. Furthermore, Example 7 and Comparative Example 5 were added to each well and cultured under the condition of 37° C. and 5% $CO_2$. Furthermore, culturing without adding either solution of the present disclosure or paclitaxel was also performed under the same condition (Comparative Example 3).

Figure 8:
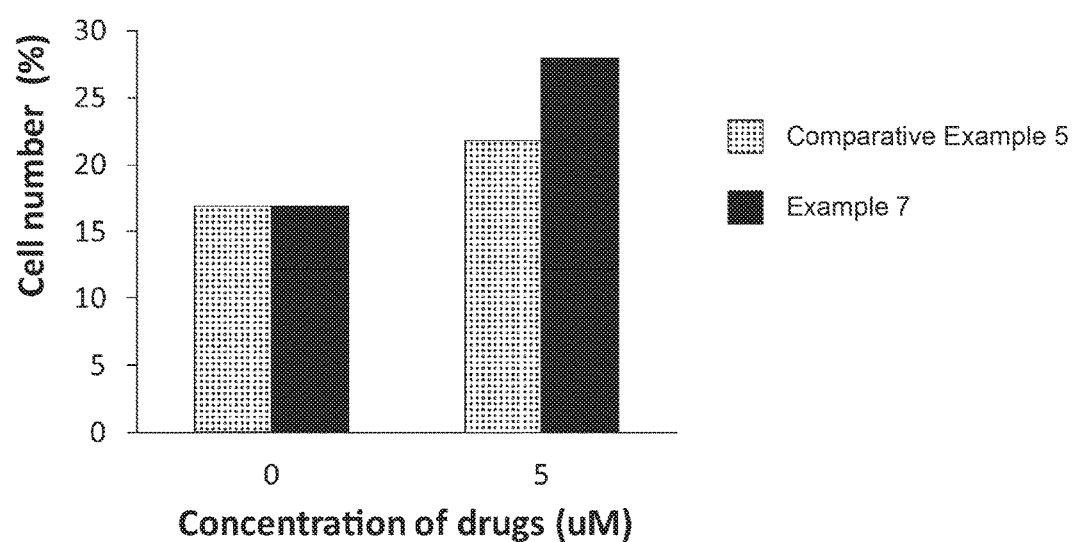
FIG. 8 is a diagram illustrating an example of the cell cycle rate of the cancer cells which the present disclosure was made to contact.

The XTT assay was performed by the same method as that of Example 4. The cell survival rate was calculated on the basis of the results of the absorbance measurement. FIG. 8 shows cell cycle rates in the G2/M phase of Example 7, Comparative Example 3, and Comparative Example 5, which were measured with a flow cytometer. Incidentally, a graph of 0 μM is Comparative Example 3 in FIG. 8.

Figure 9B:
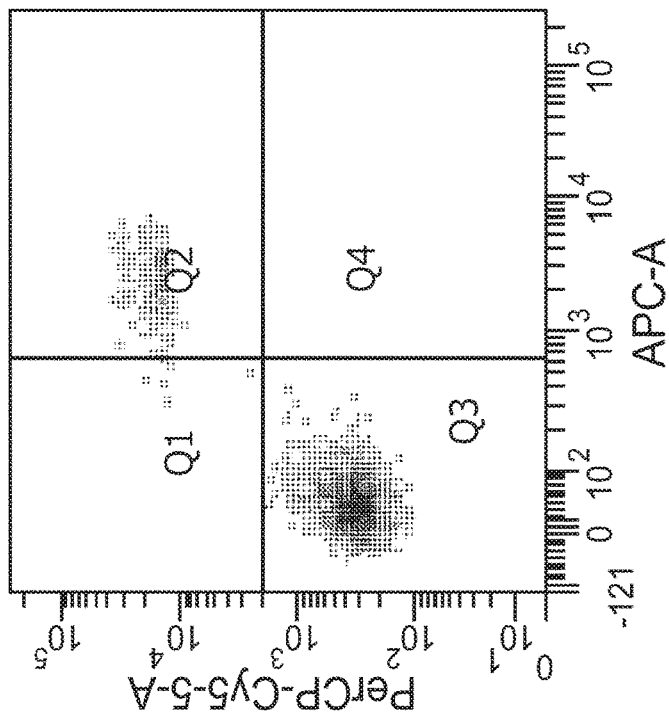
FIGS. 9A and 9B are examples of analysis results of flow cytometry of the present disclosure.
Figure 9A:
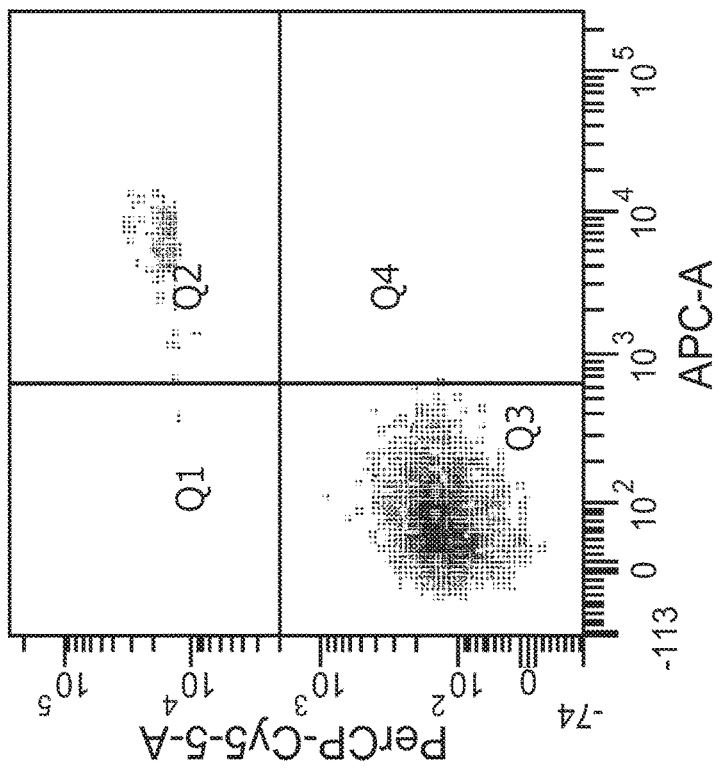

[Apoptosis Induction Check Assay]
1. Cancer Cell Line: Cancer Cell Line (MDA-MB-453) (G0/G1 Phase: 80%) for Triple-Negative Breast Cancer The above-mentioned MDA-MB-453 was assigned by RIKEN.
2. Flow Cytometry:

FACScan (BD FACSCanto™ II) was used as a flow cytometry. Cycletest™ Plus DNA Reagent Kit (BD Biosciences) was used as a reagent. BD FACSDiva™ software (BD Biosciences) was used as data analysis software. Detailed experiment procedures were performed in accordance with experiment protocol of the device manufacturer or the reagent manufacturer. Reference was also made to Reference 1 mentioned earlier. A solution of the complex of the dimer iron-salen complex and Taxol (registered trademark) (alias: paclitaxel) which was obtained in Example 2 (hereinafter referred to as "Example 2"), and a solution of Taxol (registered trademark) (alias: paclitaxel) were prepared by adjusting them with physiological saline so that their concentrations became 15 µM respectively. FIG. 9 show analysis results of the flow cytometry. Referring to FIG. 9, FIG. 9A shows the results of the assay performed by adding the solution of Taxol (registered trademark) (alias: paclitaxel). FIG. 9B shows the results of the assay performed by adding the solution of Example 2.

[MRI Contrast Effect 1]

Figure 10:
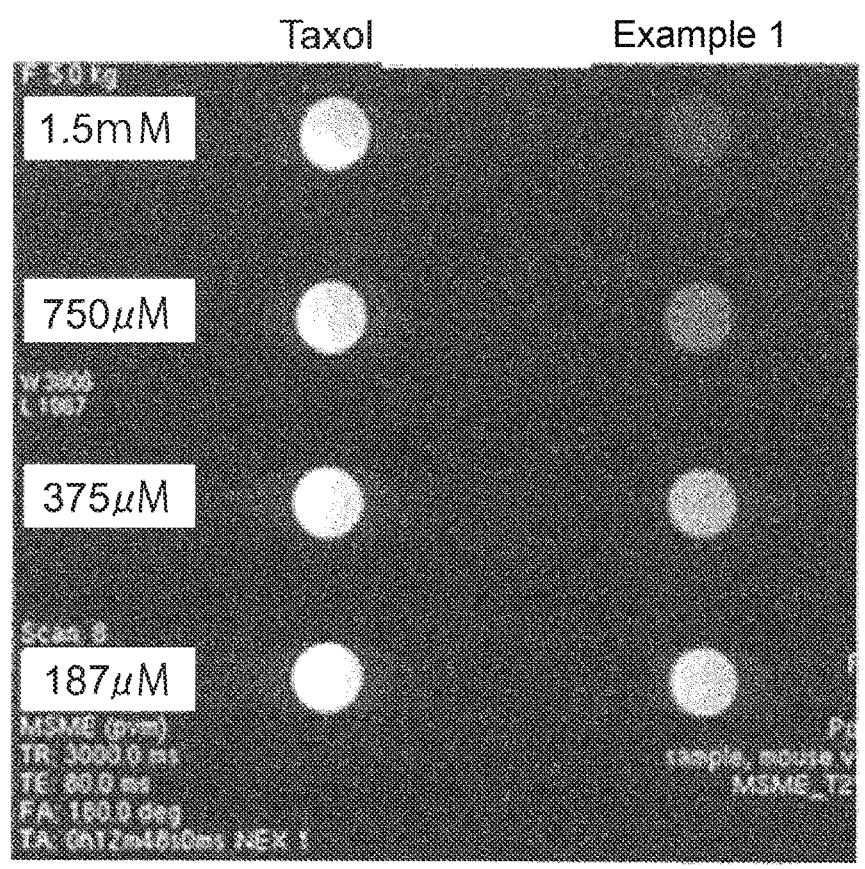
FIG. 10 is a diagram illustrating an example of MRI contrast effects of the present disclosure.

Images of Taxol (registered trademark) (alias: paclitaxel) which is a commercially available drug, and the aqueous solution of the complex obtained in Example 1 in which the monomer iron-salen complex was made to bind to paclitaxel were taken by using an MRI (7.0T by Burker) installed at Molecular Imaging Center of National Institute of Radiological Sciences. Concentrations of the aqueous solutions were 1.5 mM, 750 µM, 375 µM, and 187 µM. FIG. 10 is a T2 enhanced image taken by the above-mentioned MRI system.

Referring to FIG. 10, Taxol showed a white, high signal at every concentration. On the other hand, Example 1 with a lower concentration and a larger amount of water showed a clearer white color. As the concentration became higher, the while color became dull. Accordingly, by administering the present disclosure to the object to be imaged, quantities of moisture, blood, fat, etc. existing in an imaged region could be confirmed. Specifically speaking, it was confirmed that the complex of the monomer metal-salen complex and paclitaxel could function as an MRI contrast agent.

[MRI Contrast Effect 2]

Figure 11:
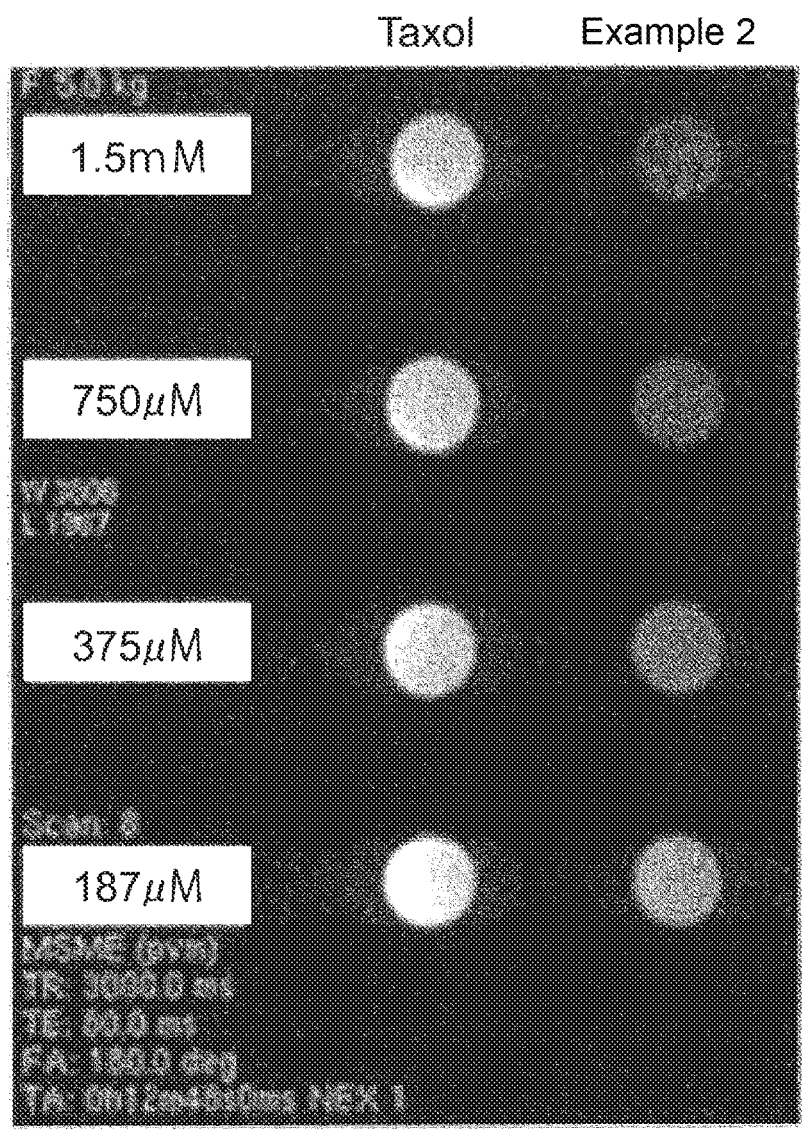
FIG. 11 is a diagram illustrating an example of MRI contrast effects of the present disclosure.

Images of Taxol (registered trademark) which is the commercially available drug, and the aqueous solution were taken by using the MRI. FIG. 11 is a T2 enhanced image taken by the above-mentioned MRI system.

Referring to FIG. 11, Taxol showed a white, high signal at every concentration. On the other hand, Example 2 with a lower concentration and a larger amount of water showed a clearer white color. As the concentration became higher, the while color became dull. Accordingly, by administering the present disclosure to the object to be imaged, quantities of moisture, blood, fat, etc. existing in an imaged region could be confirmed. Specifically speaking, it was confirmed that the complex of the dimer metal-salen complex and paclitaxel could function as an MRI contrast agent.

The invention claimed is:
1. An anti-cancer agent, comprising:
a complex produced by making a metal-salen complex compound, which includes a central metal and N, N, O, O as a quadridentate ligand and is magnetic, the metal-salen complex compound binding to taxane molecules which are anticancerous,
wherein the anti-cancer agent is to kill cancer cells regarding which phase transition occurs between phases including Gap1, Synthesis, Gap2, and Mitosis and Cytokinesis, and
wherein the cancer cells are cancer cells of breast cancer or triple-negative breast cancer.

2. The anti-cancer agent according to claim 1, wherein the taxane molecules are selected from either one of paclitaxel and docetaxel.

3. The anti-cancer agent according to claim 1, wherein the metal-salen complex compound is represented by the following formula (1) bind to the taxane molecules:

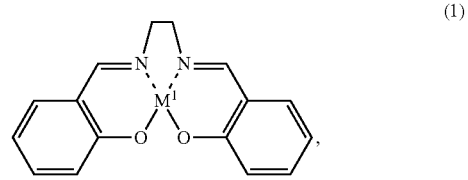

(1)

wherein in formula (1), a central metal $M^1$ is of any one type selected from a group consisting of Fe, Cr, Mn, Co, Ni, Mo, Ru, Rh, Pd, W, Re, Os, Ir, Pt, Nd, Sm, Eu, and Gd.

4. The anti-cancer agent according to claim 1, wherein the metal-salen complex compound is represented by the following formula (2) bind to the taxane molecules:

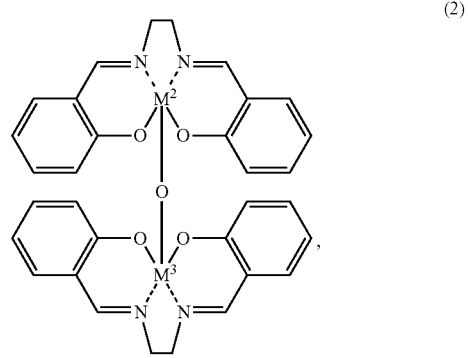

(2)

wherein in formula (2), a central metal $M^2$ and a central metal $M^3$ are independent of each other and are of any one type selected from a group consisting of Fe, Cr, Mn, Co, Ni, Mo, Ru, Rh, Pd, W, Re, Os, Ir, Pt, Nd, Sm, Eu, and Gd.

5. The anti-cancer agent according to claim 1, wherein a central metal of the metal-salen complex compound is Fe.

6. The anti-cancer agent according to claim 1, wherein the complex is represented by the following formula (3):

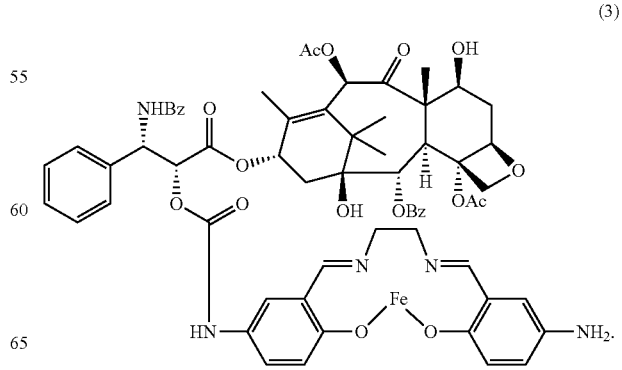

(3)

7. The anti-cancer agent according to claim 1, wherein the complex is represented by the following formula (4):

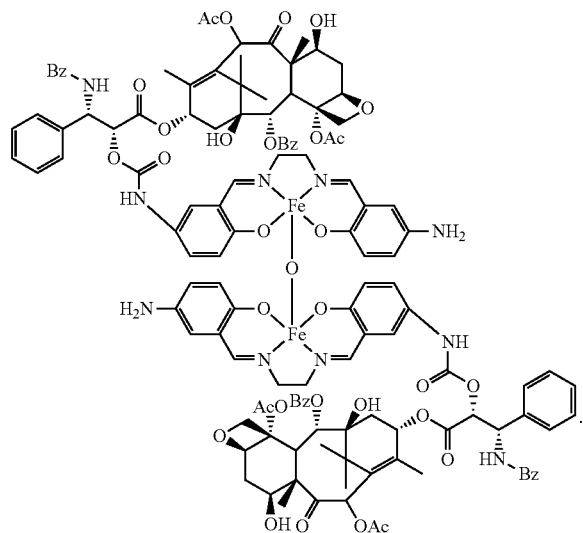

(4)

8. A cancer cell killing method to kill cancer cells, the cancer cell killing method comprising:

preparing an anti-cancer agent containing a complex produced by making a metal-salen complex compound, which includes a central metal and N, N, O, O as a quadridentate ligand and is magnetic, the metal-salen complex compound binding to taxane molecules which are anticancerous that contacts the cancer cells in any two or more continuous phases selected from a group consisting of Gap1, Synthesis, Gap2, and Mitosis and Cytokinesis, wherein the cancer cells are cancer cells of breast cancer or triple-negative breast cancer.

9. The cancer cell killing method according to claim 8, wherein the anti-cancer agent is made to contact the cancer cells by applying an external magnetic field to affected site tissues and making the anti-cancer agent indwell in the cancer cells constituting the affected site tissues.

* * * * *